US00PP30146P2

(12) United States Plant Patent
Spring et al.

(10) Patent No.: US PP30,146 P2
(45) Date of Patent: Jan. 29, 2019

(54) ***FORSYTHIA* PLANT NAMED 'BJ2013'**

(50) Latin Name: ***Forsythia* x *intermedia***
Varietal Denomination: BJ2013

(71) Applicants: Jason Jon Spring, Dillsburg, PA (US); Charles William Henry, Mount Joy, PA (US)

(72) Inventors: Jason Jon Spring, Dillsburg, PA (US); Charles William Henry, Mount Joy, PA (US)

( * ) Notice: Subject to any disclaimer, the term of this patent is extended or adjusted under 35 U.S.C. 154(b) by 0 days.

(21) Appl. No.: 15/731,802

(22) Filed: Aug. 3, 2017

(51) Int. Cl.
*A01H 5/02* (2018.01)

(52) U.S. Cl.
USPC ..... Plt./230

(58) Field of Classification Search
USPC ..... Plt./226, 230
See application file for complete search history.

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

A new and distinct *Forsythia* cultivar named 'BJ2013' which is characterized by the combination of an upright to arching growth habit with a globular plant form, a moderate abundance of small yellow flowers in early spring prior to the emergence of new foliage, unique juvenile foliage color comprised of a highly variable combination of yellow-green and light green-yellow mottle variegation on some portion of the leaf surface with the balance of the leaf with zonal green-yellow coloration, unique mature foliage variegation comprised of a combination of green with light green and white mottling and zonal white coloration, and the stability of these characteristics from generation to generation.

4 Drawing Sheets

Latin name of the genus and species: The Latin name of the genus and species of the novel variety disclosed herein is *Forsythia* x *intermedia.*

Variety denomination: The inventive cultivar of *Forsythia* disclosed herein has been given the variety denomination 'BJ2013'.

BACKGROUND OF THE INVENTION

Parentage: 'BJ2013' originated as a naturally-occurring branch mutation of *Forsythia* x *intermedia* (unnamed and unpatented) at a commercial office building complex in Mechanicsburg, Pa. In 2013, the inventors discovered a branch mutation of *Forsythia* x *intermedia* which exhibited green and white leaf variegation in an irregular mottle pattern with white zonal coloration. Cuttings were taken from the mutated branch, rooted, and then grown to a mature size to confirm the distinctness and stability of the traits first observed. In April of 2017, the unique variegation of the claimed plant was determined to be stable and suitable for commercial introduction. The plant was given the name, 'BJ2013'.

Asexual Reproduction: Asexual reproduction of 'BJ2013', by way of softwood stem tip cuttings, was first performed in 2013 in Mechanicsburg, Pa. Through two subsequent generations, the unique features of this cultivar have proven to be stable and true to type.

SUMMARY OF THE INVENTION

The cultivar 'BJ2013' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BJ2013'. These characteristics in combination distinguish 'BJ2013' as a new and distinct *Forsythia* x *intermedia* cultivar:

1. *Forsythia* 'BJ2013' exhibits an upright to arching growth habit with a globular plant form; and
2. *Forsythia* 'BJ2013' exhibits juvenile foliage color comprised of a highly variable combination of yellow-green and light green-yellow mottle variegation on some portion of the leaf surface, with the balance of the leaf with zonal green-yellow coloration; and
3. *Forsythia* 'BJ2013' exhibits mature foliage color comprised of a highly variable combination of dark yellow-green and light yellow-green and white mottle variegation on some portion of the leaf surface, with the balance of the leaf with zonal white coloration; and
4. *Forsythia* 'BJ2013' exhibits stable foliage variegation, with mature foliage which does not revert to a solid green coloration.

BOTANICAL DESCRIPTION OF THE PLANT

Figure 1:
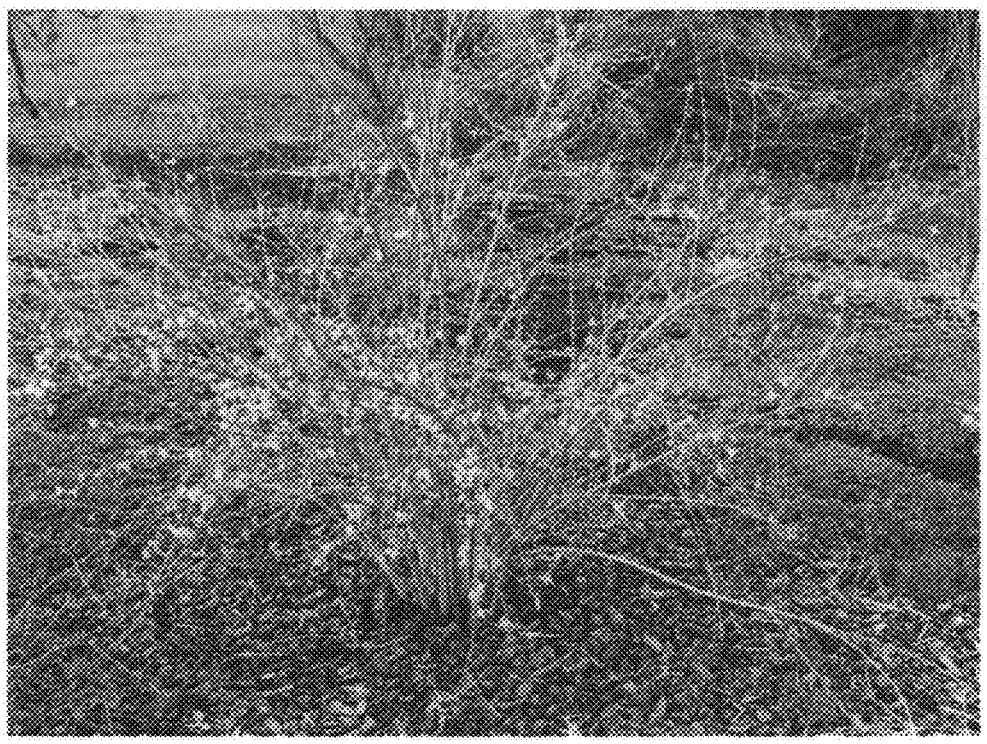
FIG. 1 illustrates, as nearly true as it is reasonably possible to make the same in color photographs of this type, an exemplary 'BJ2013' plant in flower, at approximately 3 years old, grown outdoors in Mechanicsburg, Pa.
Figure 2:
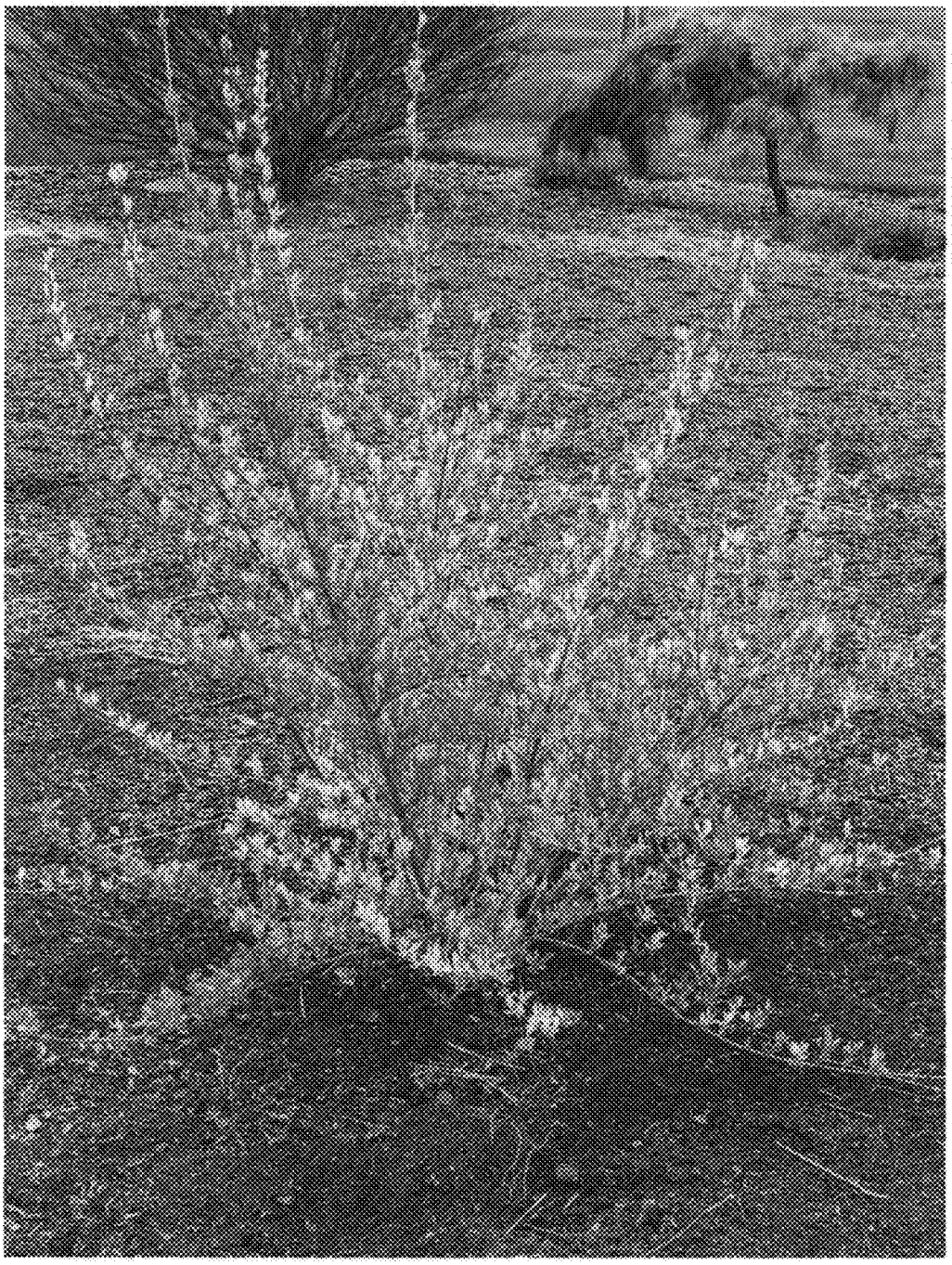
FIG. 2 illustrates, as nearly true as it is reasonably possible to make the same in color photographs of this type, an exemplary 'BJ2013' plant with newly emerged juvenile foliage, at approximately 3 years old, grown outdoors in Mechanicsburg, Pa.
Figure 3:
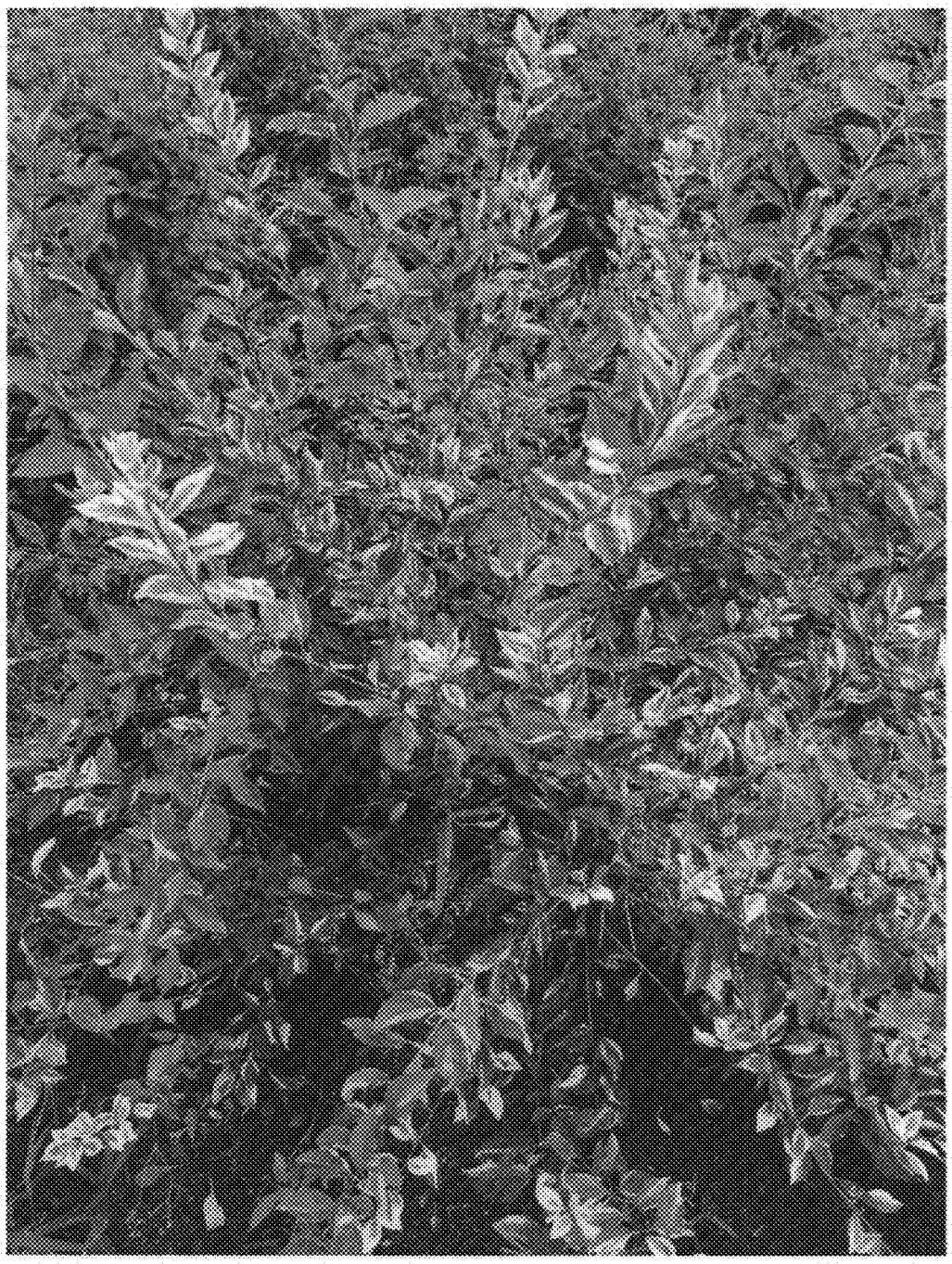
FIG. 3 illustrates, as nearly true as it is reasonably possible to make the same in color photographs of this type, an exemplary 'BJ2013' plant with mature foliage, at approximately 2.5 years old, grown outdoors in Mechanicsburg, Pa.
Figure 4:
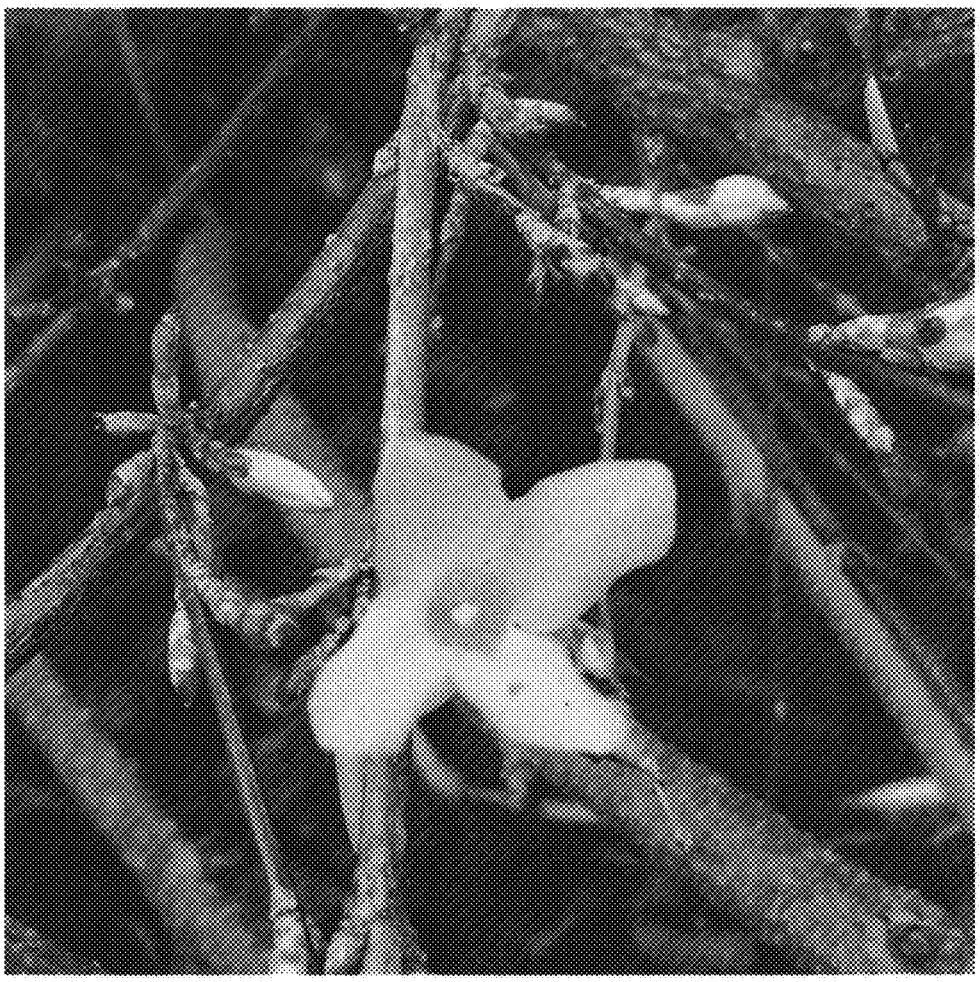
FIG. 4 illustrates, as nearly true as it is reasonably possible to make the same in color photographs of this type, exemplary flower bud and flower of 'BJ2013'.

The following observations and measurements made in May of 2017 and, unless otherwise indicated, describe a one year old potted 'BJ2013' plant grown outdoors in Mechanicsburg, Pa. Plants were grown in full sun and without irrigation or fertilization. No chemical pest or disease measures were utilized in production. Those skilled in the art will appreciate that certain characteristics will vary with older or, conversely, with younger plants. 'BJ2013' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 1986 edition.

A botanical description of 'BJ2013' and comparisons with the parent plant and most similar commercial *Forsythia* cultivar known to the inventor are provided below.

Plant description:

*Growth habit*.—Deciduous flowering shrub with an upright to arching growth habit.

*Plant shape*.—Globular.

*Average height*.—Approximately 250 cm when fully matured.

*Average width*.—Approximately 250 cm when fully matured.

*Plant vigor*.—Vigorous.

*Propagation details*.—Asexual propagation may be accomplished by softwood stem cuttings.

*Time to initiate roots*.—Approximately 21 to 28 days are required to initiate roots from a softwood cutting.

*Time to produce a marketable rooted cutting*.—Approximately 12 weeks when propagated in the spring.

*Time to produce a marketable finished plant*.—Approximately 12 months in a 3 gallon nursery container.

*Disease and pest resistance or susceptibility*.—Neither susceptibility nor resistance to normal diseases and pests of *Forsythia* has been observed.

*Environmental tolerances*.—Adapt to USDA Zones 5 to 8; drought resistant once established; tolerant of full sun exposure.

Root system:

*General*.—Deep rooted tap root bearing fibrous lateral roots; freely branched and moderately dense rooting.

*Distribution in the soil profile*.—Shallow to deep.

*Texture*.—Fleshy

*Color*.—Juvenile roots are nearest to orange-white, RHS 158C; mature roots are nearest to greyed-orange, RHS 165B.

Stems:

*Branching habit*.—Basally branched with a plurality of main stems, themselves freely branching, and giving rise to numerous lateral branches.

*Main stem*.—Attitude — Erect to arched. Cross section — Round. Diameter — 10 mm. Color — Greyed-yellow, nearest to a combination of RHS 161A and 162D. Texture — Lenticels develop into fissures of varying length (up to 5 mm long) as branches mature; color of the fissures is Brown, RHS 200C.

*Lateral branches*.—Aspect — Average angle is approximately 40 degrees from main stem. Cross section — Quadrangulate. Strength — Strong. Length of lateral branches — 28.5 cm. Diameter of lateral branches — Averaging 4.0 mm at the base. Internode length on lateral branches — Average of 6.5 cm. Texture, pubescence and luster of lateral branches — Smooth with the exception of lenticels, glabrous, and matte; becoming woody with age. Color, juvenile — Yellow-green, RHS 145A, and suffused with Greyed-Red on the adaxial surface, RHS 182C. Color, mature — Greyed-yellow, nearest to a combination of RHS 161A and 162D. Lenticels — Elliptical; approximately 1 mm long, 0.25 to 0.5 mm wide, and 0.25 mm high; Greyed-brown, RHS 199D. Lenticels develop into fissures of varying length (up to 5 mm long) as branches mature; color of the fissures is Brown, RHS 200C.

Foliage:

*Arrangement*.—Opposite.

*Attachment*.—Petiolate.

*Division*.—Simple.

*Abundance of foliage*.—Very abundant.

*Lamina*.—Dimensions — 75 mm long and 35 mm wide, on average. Shape — Elliptic. Aspect — Slightly revolute and curled under. Apex — Acute. Base — Cuneate. Margin — Serrulate; lightly undulated. Pubescence, adaxial surface — Glabrous. Texture and luster of adaxial surface — Smooth and slightly glossy. Pubescence, abaxial surface — Glabrous. Texture and luster of abaxial surface — Smooth and slightly glossy. Color — Juvenile foliage, adaxial surface — Comprised of a highly variable combination of yellow-green and light green-yellow mottle variegation on some portion of the leaf surface, with the balance of the leaf with zonal green-yellow coloration. The presence of the green-yellow, RHS 1C, irregular zonal coloration may occur from the midrib to margin (i.e. covering one half of the leaf), or in irregular blotches bordered by the midrib, secondary veins, and leaf margins, or as broad irregular margins, or in some combination thereof. This zonal coloration fades to a lighter yellow as leaves mature, in between RHS 9D and 11D. The mottle variegation consists of yellow-green, nearest to RHS 144A, with green-yellow mottling, RHS 1C, which fades to yellow in between RHS 9D and 11D as leaves mature. Juvenile foliage, abaxial surface — Comprised of a highly variable combination of green and light green-yellow mottle variegation on some portion of the leaf surface, with the balance of the leaf with zonal green-yellow coloration. The presence of the green-yellow, RHS 1C, irregular zonal coloration may occur from the midrib to margin (i.e. covering one half of the leaf), or in irregular blotches bordered by the midrib, secondary veins, and leaf margins, or as broad irregular margins, or in some combination thereof. This zonal coloration fades to a lighter yellow as leaves mature, in between RHS 9D and 11D. The mottle variegation consists of green, nearest to RHS 138B, with green-yellow mottling, RHS 1C, which fades to yellow in between RHS 9D and 11D as leaves mature. Mature foliage, adaxial surface — Comprised of a highly variable combination of dark yellow-green and light yellow-green to white mottle variegation on some portion of the leaf surface, with the balance of the leaf with zonal white coloration. The presence of the white, RHS 155A, irregular zonal coloration may occur from the midrib to margin (i.e. covering one half of the leaf), or in irregular blotches bordered by the midrib, secondary veins, and leaf margins, or as broad irregular margins, or in some combination thereof. The mottle variegation consists of yellow-green, nearest to RHS 144A, with lighter yellow-green, nearest to RHS 144D, and white mottling, RHS 155A. Mature foliage, abaxial surface — Comprised of a highly variable combination of yellow-green and white mottle variegation on some portion of the leaf surface, with the balance of the leaf with zonal white coloration. The presence of the white, RHS 155A, irregular zonal coloration may occur from the midrib to margin (i.e. covering one half of the leaf), or in irregular blotches bordered by the midrib, secondary veins, and leaf margins, or as broad irregular margins, or in some combination thereof. The mottle variegation consists of yellow-green, nearest to RHS 144B, with lighter yellow-green, nearest to RHS 144D, and white mottling, RHS 155A. Venation — Pattern — Pinnate. Color, adaxial surface — Yellow-green, nearest to in between RHS 144A and 144B, where mottle variegation is present; white, RHS 155A, where zonal coloration is present. Color, abaxial surface — Yellow-green, nearest to in between RHS 144A and 144B, where mottle variegation is present; white, RHS 155A, where zonal coloration is present.

*Petiole*.—Length — 12 mm. Width — 1.5 mm. Cross section — Sulcate. Texture — Glabrous; smooth. Luster — Matte. Strength — Strong. Color, adaxial surface — Yellow-green, RHS 145A. Color, abaxial surface — Yellow-green, RHS 145A.

*Stipule*.—Shape — Globular. Apex — Acute. Length — 0.5 mm. Width — 0.25 mm. Texture — Glabrous; smooth. Luster — Matte. Color, adaxial surface — Yellow-green, RHS 145A. Color, abaxial surface — Yellow-green, RHS 145A.

Inflorescence:

*Type*.—Flowers are solitary; two opposing flowers are borne axially.

*Natural flowering season*.—Early spring in Mechanicsburg, Pa.

*Flowering habit*.—Not repeating; moderately floriferous.

*Peduncle*.—Attitude — At an angle of approximately 30 degrees from lateral branch. Cross section — Round. Dimensions — 5 mm long and 0.75 mm wide. Color — Yellow-green, nearest to RHS 145A. Texture — Glabrous, smooth. Strength — Moderately strong.

Flower buds:

*Bud shape*.—Narrow oblong with an acute apex.

*Bud dimensions*.—4.0 to 5.0 mm long and 2.0 to 2.5 mm in diameter.

*Bud color*.—Yellow-green, RHS 144C.

Flower:

*Flower habit*.—Perfect; complete.

*Flower shape*.—Funnelform to salverform flowers with a single whorl of 6 true petals fused at the base and several inner whorls comprised of 10 to 12 petaloids.

*Lastingness*.—Approximately 2 weeks.

*Persistence*.—Not persistent.

*Flower aspect*.—Outward to upright.

*Fragrance*.—None detected.

*Calyx*.—Calyx shape — Synsepalous, cupped at the base with 4 sepal lobes arranged in a star shape. Calyx dimensions — 15 mm in diameter and 30 mm deep, including sepal lobes. Perianth dimensions — 1.5 to 2.0 cm in diameter and 1.5 cm tall. Sepals — Sepal arrangement — Rotate; fused at the base with 4 ovate sepal lobes. Number of sepal lobes — 4. Sepal lobe dimensions — 3.0 mm long and 2.0 mm wide. Sepal lobe shape — Ovate. Sepal lobe margins — Entire; not undulated. Sepal lobe apex — Acute. Sepal base — Fused. Sepal texture — Smooth; glabrous. Sepal color, inner surface — Yellow-green, nearest to RHS 145C. Sepal color, outer surface — Yellow-green, nearest to RHS 145C.

*Corolla*.—Petal and petaloid arrangement — Rotate with petals arranged in a single outer whorl; fused at the base, forming a short corolla tube of approximately 8.0 mm deep and 4.0 mm in diameter. Petals — Quantity — 4. Fused or unfused — Fused at the base. Dimensions of free portion of the petal — Approximately 10 mm long and 4.0 mm wide. Shape — Oblong. Apex — Obtuse. Base — Fused. Aspect — Revolute and reflexed. Margin — Entire; undulated. Texture — Glabrous. Luster — Matte to satiny. Color when opening (upper side) — Yellow, nearest to RHS 12A. Color when opening (under side) — Yellow, nearest to RHS 12A. Color when fully opened (upper side) — Yellow, nearest to RHS 12A. Color when fully opened (under side) — Yellow, nearest to RHS 12A. Color fading to — Not fading.

Reproductive organs:

*Androecium*.—Stamen quantity — 2. Filament — Dimensions — Approximately 8.0 mm long and 0.25 to 0.5 mm in diameter. Color — Yellow, nearest to RHS 13B. Attachment — Epipetalous; adnate to the corolla. Anther — Anther attachment — Basifixed. Anther shape — Oblong. Anther size — 1.0 to 2.0 mm long and 1.0 mm in diameter. Anther color — Yellow, nearest to RHS 13B. Pollen — Amount of pollen — Moderately abundant. Pollen color — Yellow, RHS 11A.

*Gynoecium*.—Pistil quantity — One. Stigma — Shape — Round. Dimensions — Approximately 1.5 mm across and 1.0 to 1.25 mm tall. Color — Yellow-green, RHS 144D. Style — Dimensions — 3.0 mm long and 0.75 mm in diameter. Color —

Yellow-green, RHS 145C. Ovary — Position — Superior. Shape — Globose. Dimensions — 3.0 mm long and 2.0 mm wide. Color — Yellow-green, RHS 144C.

Seed and fruit: Not observed.

COMPARISON WITH THE PARENT PLANT

Plants of the new cultivar 'BJ2013' may be distinguished from its parent, *Forsythia* x *intermedia* (unnamed and unpatented), by the characteristics described in Table 1.

TABLE 1

| Characteristic | 'BJ2013' | *Forsythia* x*intermedia* |
|---|---|---|
| Leaf variegation. | A combination of mottling and irregular zonal white colorations. | None. |

COMPARISON WITH THE CLOSEST KNOWN COMMERCIAL COMPARATOR

Plants of the new cultivar 'BJ2013' can be distinguished from the commercial variety, *Forsythia* x *intermedia* 'Variegata' (not patented), by the characteristics described in Table 2.

TABLE 2

| Characteristic | 'BJ2013' | 'Variegata' |
|---|---|---|
| Leaf variegation expression, mature leaves. | A variable combination of green and white or light green mottling, and zonal white coloration. | Green and light yellow mottling variegation; occasionally margined withlight yellow. |
| Stability of leaf variegation, | Stable; maintains variegation, | Not stable; variegated foliage may revert to green. |

That which is claimed is:

1. A new and distinct cultivar of *Forsythia* plant named 'BJ2013', substantially as described and illustrated herein.

* * * * *